United States Patent
Orten

(10) Patent No.: US 6,741,719 B1
(45) Date of Patent: May 25, 2004

(54) HEAD PHONE

(75) Inventor: Birger Orten, Alesund (NO)

(73) Assignee: Meditron AS, Vettre (NO)

( * ) Notice: Subject to any disclaimer, the term of this patent is extended or adjusted under 35 U.S.C. 154(b) by 0 days.

(21) Appl. No.: 09/744,353

(22) PCT Filed: Jul. 15, 1999

(86) PCT No.: PCT/NO99/00237

§ 371 (c)(1),
(2), (4) Date: Mar. 6, 2001

(87) PCT Pub. No.: WO00/08893

PCT Pub. Date: Feb. 17, 2000

(30) Foreign Application Priority Data

Jul. 24, 1998 (NO) .......................................... 19983424

(51) Int. Cl.[7] ................................................ H04R 25/00
(52) U.S. Cl. ...................................... 381/380; 381/382
(58) Field of Search ................................ 381/370–371, 381/378, 380, 381–382, 327–328, 330, 374, 375, 377, 379, 338–339; 181/129, 130, 135; 379/430

(56) References Cited

U.S. PATENT DOCUMENTS

| | | | | | |
|---|---|---|---|---|---|
| 454,138 | A | * | 6/1891 | Mercadier | 381/370 |
| 582,901 | A | * | 5/1897 | Dennis | 181/136 |
| 1,624,144 | A | * | 4/1927 | Mathieu | 181/129 |
| 1,747,778 | A | * | 2/1930 | Kuchenmeiser | 381/370 |
| 2,363,175 | A | * | 11/1944 | Grossman | 381/322 |
| 2,584,402 | A | * | 2/1952 | Volkmann | 181/129 |
| 2,586,644 | A | * | 2/1952 | Gilbert | 381/382 |
| 2,681,389 | A | * | 6/1954 | Shaper | 381/151 |
| 2,778,889 | A | * | 1/1957 | Hausdorf | 381/338 |
| 3,160,717 | A | * | 12/1964 | Beguin | 128/867 |
| 3,301,253 | A | * | 1/1967 | Glorig | 128/866 |
| 3,469,651 | A | * | 9/1969 | Mendelson et al. | 181/135 |
| 3,671,685 | A | * | 6/1972 | McCabe | 381/338 |
| 4,048,444 | A | | 9/1977 | Giampapa | |
| RE29,487 | E | | 12/1977 | Gardner, Jr. | |
| 4,243,851 | A | * | 1/1981 | Forney | 2/423 |
| 4,347,911 | A | | 9/1982 | Bertagna et al. | |
| 4,456,797 | A | * | 6/1984 | Olsen | |
| 4,875,233 | A | * | 10/1989 | Derhaag et al. | 379/430 |
| 4,972,491 | A | * | 11/1990 | Wilcox, Jr. | 379/430 |
| 5,696,831 | A | | 12/1997 | Inanaga et al. | |
| 5,792,998 | A | | 8/1998 | Gardner, Jr. et al. | |

FOREIGN PATENT DOCUMENTS

| | | |
|---|---|---|
| DE | 325693 | 11/1975 |
| DE | 3529748 | 3/1987 |
| DK | 146990 | 2/1984 |
| WO | WO9820820 | 5/1998 |

OTHER PUBLICATIONS http//:famona.tripod.com/ent/cummings/cumm179.pdf, "Chapter 179: Amplification Devices for the Hearing–Impaired Individual" Francis K. Kuk.

* cited by examiner

Primary Examiner—Huyen Le
Assistant Examiner—P. Dabney
(74) Attorney, Agent, or Firm—Ladas & Parry

(57) ABSTRACT

A head phone comprises at least one loudspeaker of the type that rests on the outside of a user's ears, mounted on and held in place by a support. The loud speakers are equipped with a sound-concentrating duct that may be pivotable relative to the auditory canal of a user's ear so as to facilitate insertion of the duct a short distance into the auditory canal.

6 Claims, 4 Drawing Sheets

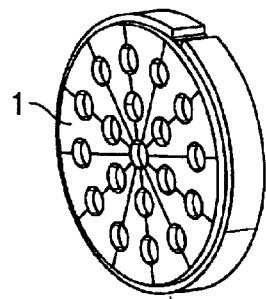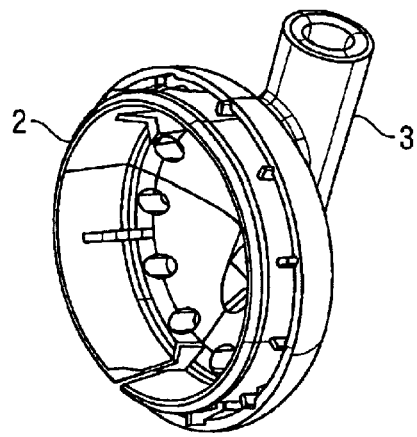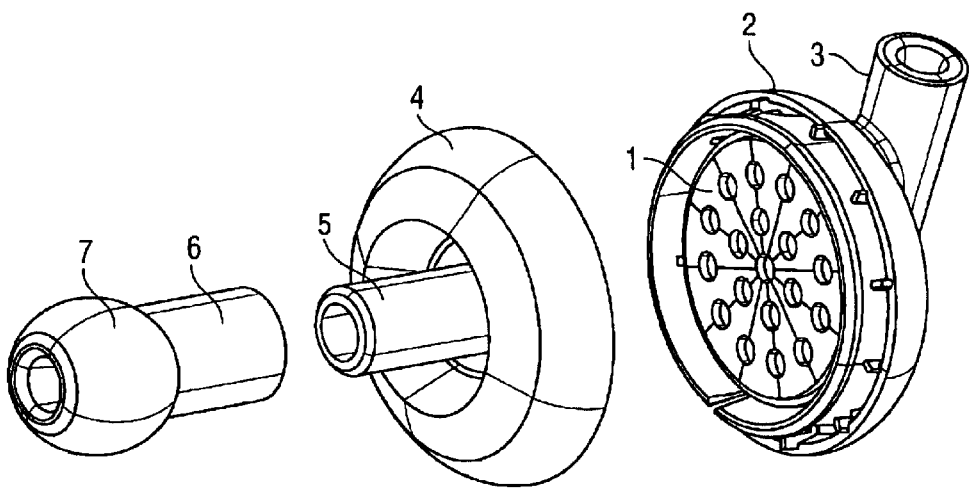

HEAD PHONE

Figure 2:
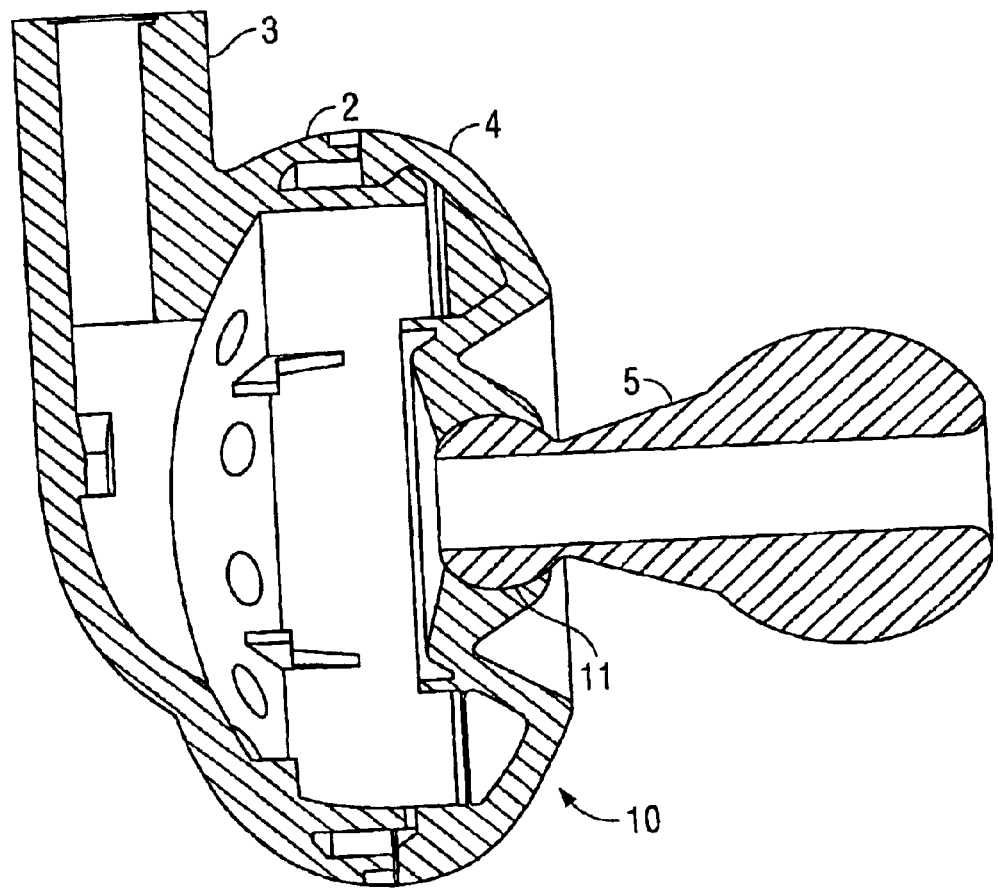

The present invention relates to new a head phone design. More particularly, the invention concerns a head phone with support means for one or two loudspeaker units, and the loudspeaker unit or units is/are of the type resting on the outside of the user's ear/ears.

Head phones are previously known in various embodiments, both with regard to transducer principle (e.g. dynamic types, electrostatic types), with regard to attachment means (e.g. head bow, self-supporting ear plug) and with regard to type of acoustical coupling to the user's ear (e.g. closed type, open type, ear plug type).

The present application deals substantially with the last mentioned field, that is the acoustical coupling manner from the sound transducer to the user's auditory canal.

Particularly within the field of auscultation, and specially in electronic auscultation using an amplified presentation of sounds picked up from e.g. a human body, it is important to use a light and comfortable head phone that is nevertheless capable of good transmission of a complete frequency range. In this connection low frequencies are of interest, but it is a disadvantage to have to rely on particularly heavy and large loudspeaker transducers.

A "double action" head phone is previously known from U.S. Pat. No. 5,333,206, in which head phone there is arranged, in addition to an "ordinarily" arranged loudspeaker element for open engagement on the outside of the user's ear, a small supplementary element extending somewhat into the auditory canal, to produce treble frequencies therein. For the rest, this design is however of a traditional outside and open type, and it needs relatively large transducers to provide a good bass response.

The present invention aims at providing good coupling of particularly the lower frequencies into the auditory canal from a conventionally supported head phone that may be of markedly light type.

Thus, in accordance with the invention there is provided a head phone comprising at least one, preferably two loudspeaker units of the type resting on the outside of the user's ear, as well as a support means for the loudspeaker unit, e.g. a head bow. The head phone in accordance with the invention is characterised in that each loudspeaker unit is equipped on its sound transmission side with a sound concentrating duct arranged to be placed a short distance into the auditory canal when in use.

In a favourable embodiment of the head phone in accordance with the invention, the sound concentrating duct is made at least partly of a flexible material, for adaptation to the user's ear.

The sound-concentrating duct may be provided with an elastic sealing material for sealing against the edge of the auditory canal.

In a favourable embodiment the sound-concentrating duct is substantially funnel-shaped, attached around the sound producing area of the loudspeaker unit and tapered in toward the user's ear.

In a further favourable embodiment, the loudspeaker units may be pivotably mounted on the support means, for adaptation to the user in question.

Besides, in a favourable embodiment the sound concentrating duct may be equipped, near the sound transmission side of the loudspeaker unit, with a ball joint for adapting the angle of the sound concentrating duct toward the ear of the particular user.

In another aspect of the invention, there is provided an electronic stethoscope comprising a sound sensor unit for picking up body sounds and converting such sounds into electrical signals, an amplifying and processing unit for these signals, as well as a head phone that comprises at least one, preferably two loudspeaker units of the type that rests on the outside of the user's ear(s) and a support means for the loudspeaker unit(s), e.g. a head bow. The stethoscope in accordance with the invention is characterised in that each loudspeaker unit is equipped with a sound-concentrating duct on its sound transmission side, arranged to be placed a short distance into the auditory canal when in use.

Figure 3:
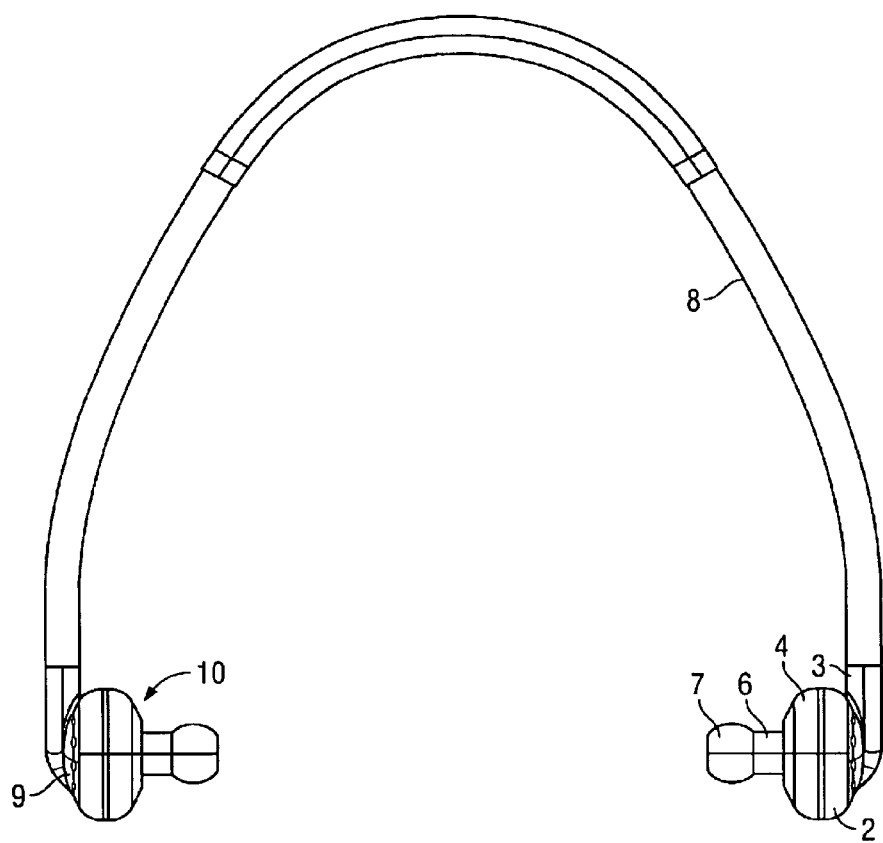
Figure 4:
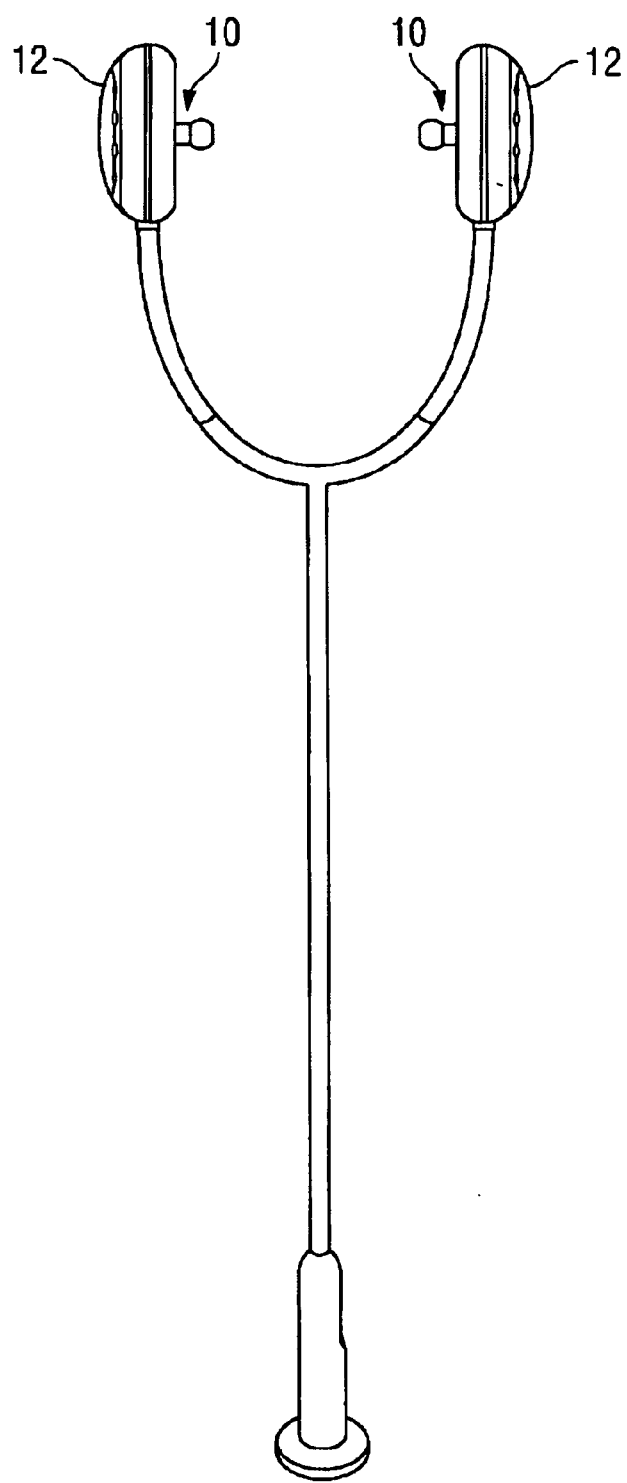

In the following the invention shall be discussed in further detail, and with reference to the embodiment example appearing from the appended drawings, wherein FIG. 1a shows a loudspeaker transducer, FIG. 1b shows the main part of a loudspeaker housing FIG. 1c shows the parts of FIG. 1a and FIG. 1b mounted together, FIG. 1d shows a closure part for the loudspeaker housing FIG. 1e shows an ear plug, FIG. 2 shows an arrangement of a ball joint on the sound concentrating duct, FIG. 3 shows a complete head phone in accordance with the invention, and FIG. 4 shows a complete head phone as used in a stethoscope and having an optional equipment in the form of ear bells on the outside of the loudspeaker units for closing out disturbing external sounds.

Ear phones constructed to reproduce sound with hi-fi quality or almost hi-fi quality, are known in two main forms, namely in the form of (a) pieces resting on the outside of the ear and having relatively large loudspeaker units, and a sealing ring surrounding the whole ear ("closed" system), or without such sealing ("open" system), and (b) pieces to be inserted into the ear and having very small loudspeaker units, typically in connection with portable radio/cassette players CD/IMD players. Also in connection with dictaphone use there is known pieces to be inserted into the ear and having very small loudspeaker units, preferably mounted on a head band or a down-hanging bow. Usually, such head phones are not capable of reproducing a complete spectrum, and in particular low frequencies are attenuated.

The present invention combines two important features, namely the feature of a large loudspeaker unit resting on the outside of the ear, and the feature of a short sound duct that is placed a short distance into the ear, and which preferably has elastic sealing material against the edge of the auditory canal. The bass response will be superior in comparison to small ear phones for portable equipment, and the sealing characteristics will be very good—little sound will leak out. Since the bass response will be good, one may, as a result of the sound duct into the ear, reduce the dimensions of the loudspeaker transducer element itself, and as a result this may provide a lighter head phone.

In FIGS. 1a–1e, embodiments are shown regarding the parts which, when mounted together, constitute a loudspeaker unit of the type that is an essential element of the head phone in accordance with the invention. FIG. 1a shows a special embodiment of a loudspeaker transducer, with reference numeral 1. A transducer 1 as shown here is of the piezoelectric type, is a trading commodity and can be supplied by e.g. the company Molex Norge. However, the invention is not limited to a special type of transducer but central features of the invention give, as mentioned above, the opportunity to utilize less heavy electro-acoustical transducers than in conventional loudspeaker units.

In FIG. 1b appears the main part of a loudspeaker housing 2, which is also equipped with an attachment part 3 to a head bow (8, see FIG. 2). The loudspeaker housing 2 is supported on the attachment part 3 by means of a pivot joint, so that the angle of the housing toward the user's head/ear can be adjusted.

In FIG. 1c the transducer 1 is shown laid into the loudspeaker housing 2, and FIG. 1c, FIG. 1d and FIG. 1e can be viewed as a whole, as an exploded view of the complete loudspeaker unit. FIG. 1d shows actually a closure part 4 for the loudspeaker housing, adapted to be threaded onto part 2 to make the housing complete. Centrally and extending out from the closure part 4 there is arranged a sound duct 5 that points in toward the auditory canal of the user. FIG. 1 shows an ear plug 6 adapted to be threaded onto the outside of the sound duct 5. The ear plug 6 is preferably made of a flexible material, both to ease the threading of the plug onto the sound concentrating duct 5, and to provide adaptation to the user's ear. Numeral 7 refers to an elastic collar to provide sealing and adaptation against is the auditory canal edge.

It is also possible to obtain further improved adaptation to the ear of the particular user, by introducing a ball joint 11 in the interface between the sound concentrating duct 5 and the closure part 4 near the loudspeaker transducer, in such a manner that the duct 5 itself can be angled relative to the rest of the loudspeaker unit 10, for instance such as shown in FIG. 2.

In the embodiment appearing from FIGS. 1d and 1e, an approximately cylinder-shaped sound concentrating duct is shown, however the duct can also just as well be designed as a funnel with a tapering shape in toward the user's ear.

FIG. 3 illustrates an embodiment of a complete head phone in accordance with the invention. Two loudspeaker units 10 are attached to a head bow 8, and reference numeral 9 refers to a pivotable support joint for the loudspeaker unit 10 on the bow attachment part 3. Thus, the user may himself adapt the alignment of the loudspeaker elements 10 in toward the ears. For the rest, the loudspeaker units 10 shown are composed of the parts shown in FIGS. 1a–1e.

FIG. 4 illustrates an alternative embodiment of a head phone that may comprise part of an electronic stethoscope, such as shown previously, including special equipment, for example, for acute use, of the loudspeakers where it may be important to shut out irrelevant external sound. To achieve this, two ear bells 12 are mounted outside the loudspeaker units 10 on the side opposite the sound producing side preferably with a "snap" mount. Soft edges on the bells 12 provide sealing around the user's ears.

The ear bells 12 shown may possibly also comprise a more advanced type with built-in "anti sound" equipment, i.e., sound-producing equipment to produce "negative or out of phase" sound adapted to nullify the irrelevant external sound. Such equipment is per se known, and will provide an even more favorable auscultation situation.

What is claimed is:

1. A head phone comprising:
   at least one loudspeaker unit of the type resting on the outside of the user's ear(s), and
   a support means for the loudspeaker unit(s), said loudspeaker unit(s) being pivotably mounted on the support means, each loudspeaker unit having a sound producing side facing the user's eat and being equipped on its sound producing side with a sound concentrating duct arranged to be placed a short distance into the auditory canal when in use, said sound concentrating duct being equipped with a ball joint near the sound producing side of the loudspeaker unit for adaptation of the angle of the sound concentrating duct toward the user's ear.

2. The head phone of claim 1, further characterized in that said sound concentrating duct is made at least partially of a flexible material for adaptation to the user's ear.

3. The head phone of claim 1, characterized in that said sound concentrating duct is provided with an elastic sealing material for sealing against the edge of the auditory canal.

4. The head phone of claim 1, further characterized in that said sound concentrating duct is funnel-shaped, and is attached around the sound producing area of said loudspeaker unit and tapered in toward the user's ear.

5. The head phone of claim 1 further characterized by a surrounding ear bell mounted on the outside of each loudspeaker unit at a side opposite from the sound producing side to shut out irrelevant external sound.

6. The head phone of claim 5, further characterized in that each ear bell has built-in equipment for producing sound adapted to nullify irrelevant external sound that may be otherwise directed toward the user's auditory canal.

\* \* \* \* \*